(12) United States Patent
Lawson et al.

(10) Patent No.: US 8,633,268 B2
(45) Date of Patent: Jan. 21, 2014

(54) SYNTHETIC POLYISOPRENE FOLEY CATHETER

(75) Inventors: Kenneth Glenn Lawson, Oxford, GA (US); Linda J. Lawson, legal representative, Oxford, GA (US); Fung Bor Chen, Greer, SC (US); Ian Capstick, Moncks Corner, SC (US); Randy Tuck, Summerville, SC (US)

(73) Assignee: C.R. Bard, Inc., Covington, GA (US)

( * ) Notice: Subject to any disclaimer, the term of this patent is extended or adjusted under 35 U.S.C. 154(b) by 261 days.

(21) Appl. No.: 12/811,439

(22) PCT Filed: Dec. 30, 2008

(86) PCT No.: PCT/US2008/088526
§ 371 (c)(1),
(2), (4) Date: Oct. 21, 2010

(87) PCT Pub. No.: WO2009/088851
PCT Pub. Date: Jul. 16, 2009

(65) Prior Publication Data
US 2011/0028943 A1  Feb. 3, 2011

Related U.S. Application Data

(60) Provisional application No. 61/019,213, filed on Jan. 4, 2008.

(51) Int. Cl.
*C08K 5/16* (2006.01)
*C08K 5/39* (2006.01)

(52) U.S. Cl.
USPC ............................ 524/198; 524/186; 524/201

(58) Field of Classification Search
USPC ........................................................ 524/189
See application file for complete search history.

(56) References Cited

U.S. PATENT DOCUMENTS

| | | | |
|---|---|---|---|
| 3,067,180 A | 12/1962 | Miller et al. | |
| 3,223,134 A | 12/1965 | Hofmann | |
| 3,718,628 A | 2/1973 | Boyer | |
| 3,965,077 A | 6/1976 | Son | |

(Continued)

FOREIGN PATENT DOCUMENTS

| | | |
|---|---|---|
| EP | 0 093 093 B2 | 11/1991 |
| EP | 0 009 15133 A1 | 5/1999 |

(Continued)

OTHER PUBLICATIONS

Senyek, M. L. 2008. "Isoprene Polymers." in: Encyclopedia of Polymer Science and Technology, pp. 56-57.*

(Continued)

*Primary Examiner* — James J Seidleck
*Assistant Examiner* — Josephine Chang
(74) *Attorney, Agent, or Firm* — Knobbe Martens Olson & Bear LLP

(57) ABSTRACT

An indwelling urinary drainage catheter (12, 110) includes synthetic polyisoprene rubber (SPIR). Advantageously, the SPIR catheter can meet the tensile and resiliency requirements of Foley applications while avoiding the risk of allergic reactions in sensitive patients. The SPIR comprises an accelerator system that uses a carbamate as the only accelerator, a guanidine as the only accelerator, a combination of guanidine and carbamate accelerators, a combination of carbamate and thiazole accelerators, or a combination of guanidine, carbamate and thiazole accelerators.

10 Claims, 4 Drawing Sheets

(56) References Cited

U.S. PATENT DOCUMENTS

| | | |
|---|---|---|
| 4,110,240 A | 8/1978 | Leo et al. |
| 4,128,539 A | 12/1978 | Onizawa |
| 4,146,689 A | 3/1979 | Onizawa |
| 4,172,939 A | 10/1979 | Hoh |
| 4,222,384 A | 9/1980 | Birtwell |
| 4,237,247 A | 12/1980 | Matoba |
| 4,248,985 A | 2/1981 | Ohishi |
| 4,271,049 A | 6/1981 | Coran |
| 4,338,410 A | 7/1982 | Ueno et al. |
| 4,588,752 A | 5/1986 | Kmiec |
| 4,687,756 A | 8/1987 | Okamoto et al. |
| 4,725,650 A | 2/1988 | Landi |
| 4,855,364 A | 8/1989 | Sandstrom |
| 4,861,842 A | 8/1989 | Cohen et al. |
| 4,870,135 A | 9/1989 | Mowdood et al. |
| 4,906,237 A | 3/1990 | Johansson |
| 4,948,840 A | 8/1990 | Berta |
| 4,983,685 A | 1/1991 | Aoshima et al. |
| 5,036,133 A | 7/1991 | Coran |
| 5,096,978 A | 3/1992 | Coran |
| 5,158,997 A | 10/1992 | Berta |
| 5,160,790 A | 11/1992 | Elton |
| 5,256,738 A | 10/1993 | Chasser et al. |
| 5,290,585 A | 3/1994 | Elton |
| 5,342,900 A | 8/1994 | Wolpers |
| 5,356,997 A | 10/1994 | Massie, II et al. |
| 5,374,689 A | 12/1994 | Rostek, Jr. |
| 5,382,629 A * | 1/1995 | Coran et al. .................. 525/194 |
| 5,473,017 A | 12/1995 | Wang |
| 5,545,451 A | 8/1996 | Haung |
| 5,554,699 A | 9/1996 | Layer et al. |
| 5,601,870 A | 2/1997 | Haung |
| 5,609,583 A | 3/1997 | Hakki et al. |
| 5,612,083 A | 3/1997 | Haung |
| 5,662,960 A | 9/1997 | Hostettler |
| 5,674,277 A | 10/1997 | Freitag |
| 5,770,632 A | 6/1998 | Sekhar et al. |
| 5,800,412 A | 9/1998 | Zhang |
| 5,869,591 A | 2/1999 | McKay |
| 5,872,173 A | 2/1999 | Anand |
| 5,876,624 A | 3/1999 | Novits et al. |
| 5,916,956 A | 6/1999 | Wang et al. |
| 5,919,570 A | 7/1999 | Hostettler |
| 6,057,044 A | 5/2000 | Rennar |
| 6,071,996 A | 6/2000 | Davis |
| 6,075,092 A | 6/2000 | Nakamura |
| 6,096,013 A | 8/2000 | Hakky et al. |
| 6,120,904 A | 9/2000 | Hostettler |
| 6,187,829 B1 | 2/2001 | Sellers |
| 6,187,857 B1 | 2/2001 | Ozawa et al. |
| 6,191,192 B1 | 2/2001 | Monden |
| 6,193,699 B1 | 2/2001 | Matsumoto |
| 6,221,447 B1 | 4/2001 | Munn |
| 6,238,799 B1 | 5/2001 | Opolski |
| 6,241,409 B1 | 6/2001 | Holloway |
| 6,329,444 B1 | 12/2001 | McGlothlin |
| 6,365,657 B1 | 4/2002 | Goto et al. |
| 6,372,856 B2 | 4/2002 | Ozawa et al. |
| 6,391,409 B1 | 5/2002 | Yeh |
| 6,420,488 B1 | 7/2002 | Penot |
| 6,422,997 B1 | 7/2002 | Green et al. |
| 6,451,893 B1 | 9/2002 | Tao |
| 6,476,154 B1 | 11/2002 | Maly |
| 6,521,691 B1 | 2/2003 | Agostini et al. |
| 6,523,585 B1 | 2/2003 | Ducci |
| 6,536,492 B2 | 3/2003 | Vasseur |
| 6,541,574 B1 | 4/2003 | Takemura |
| 6,613,831 B1 | 9/2003 | Bentley et al. |
| 6,618,861 B2 | 9/2003 | Saks et al. |
| 6,629,961 B1 | 10/2003 | Israelsson |
| 6,648,854 B1 | 11/2003 | Patterson et al. |
| 6,648,863 B2 | 11/2003 | Reever |
| 6,653,380 B2 | 11/2003 | Dzikowicz |
| 6,673,404 B1 | 1/2004 | Yeh et al. |
| 6,732,734 B2 | 5/2004 | Ogushi et al. |
| 6,747,099 B1 | 6/2004 | Novits |
| 6,753,374 B1 | 6/2004 | Hannon et al. |
| 6,756,449 B2 | 6/2004 | Benz |
| 6,828,387 B2 | 12/2004 | Wang et al. |
| 6,858,680 B2 | 2/2005 | Gunatillake |
| 6,872,763 B2 | 3/2005 | Andriolo |
| 6,894,082 B2 | 5/2005 | Brantl et al. |
| 6,916,309 B2 | 7/2005 | Fangrow, Jr. |
| 6,920,643 B2 | 7/2005 | McGlothlin |
| 6,951,897 B2 | 10/2005 | Penot |
| 6,972,307 B2 | 12/2005 | Zimmer et al. |
| 6,982,050 B2 | 1/2006 | Chauvin et al. |
| 6,984,689 B2 | 1/2006 | Penot et al. |
| 7,008,979 B2 | 3/2006 | Schottman |
| 7,025,753 B2 | 4/2006 | Reever |
| 7,040,404 B2 | 5/2006 | Brothers |
| 7,041,746 B2 | 5/2006 | Dzikowicz |
| 7,048,977 B2 | 5/2006 | Dzikowicz |
| 7,148,279 B2 | 12/2006 | Voorheis |
| 7,176,260 B2 | 2/2007 | Tao |
| 7,196,129 B2 | 3/2007 | Migliarini et al. |
| 7,279,532 B2 | 10/2007 | Sasagawa |
| 7,282,041 B2 | 10/2007 | Igarashi |
| 7,294,678 B2 | 11/2007 | McGlothlin |
| 7,368,490 B2 | 5/2008 | Patel |
| 7,374,711 B2 | 5/2008 | McGlothlin |
| 7,441,574 B2 | 10/2008 | Koster |
| 7,528,181 B2 | 5/2009 | Bailey et al. |
| 7,572,850 B2 | 8/2009 | Hetzel |
| 7,700,705 B2 | 4/2010 | Jole |
| 2001/0004653 A1 | 6/2001 | Ozawa et al. |
| 2001/0037097 A1 | 11/2001 | Cheng et al. |
| 2002/0042465 A1 | 4/2002 | Migliarini |
| 2002/0045868 A1 | 4/2002 | Reever |
| 2002/0115767 A1 | 8/2002 | Cruse |
| 2002/0160134 A1 | 10/2002 | Ogushi et al. |
| 2002/0173563 A1 | 11/2002 | Wang et al. |
| 2002/0193501 A1 | 12/2002 | Rajaraman |
| 2003/0055169 A1 | 3/2003 | Amino |
| 2003/0073977 A1 | 4/2003 | Charles |
| 2003/0088002 A1 | 5/2003 | Dzikowicz |
| 2003/0116319 A1 | 6/2003 | Brothers |
| 2003/0121659 A1 | 7/2003 | Brothers |
| 2003/0139524 A1 | 7/2003 | Hochgesang |
| 2003/0139730 A1 | 7/2003 | Bracken et al. |
| 2003/0141633 A1 | 7/2003 | McGlothlin |
| 2003/0161975 A1 | 8/2003 | Lucas |
| 2003/0175458 A1 | 9/2003 | Jain |
| 2003/0204008 A1 | 10/2003 | Campion |
| 2004/0045095 A1 | 3/2004 | Manzoni |
| 2004/0054038 A1 | 3/2004 | Andriolo |
| 2004/0059305 A1 | 3/2004 | Reever |
| 2004/0063832 A1 | 4/2004 | Dzikowicz |
| 2004/0071909 A1 | 4/2004 | McGlothlin |
| 2004/0087712 A1 | 5/2004 | Rajaraman |
| 2004/0106743 A1 | 6/2004 | Chauvin et al. |
| 2004/0133156 A1 | 7/2004 | Diaz |
| 2004/0152811 A1 | 8/2004 | Lin et al. |
| 2004/0158208 A1 | 8/2004 | Hiejima |
| 2004/0169317 A1 | 9/2004 | Wang et al. |
| 2004/0235587 A1 | 11/2004 | Sullivan |
| 2004/0241085 A1 | 12/2004 | Marx |
| 2004/0259974 A1 | 12/2004 | Scott |
| 2005/0027054 A1 | 2/2005 | Zimmer |
| 2005/0048121 A1 | 3/2005 | East et al. |
| 2005/0065249 A1* | 3/2005 | Dzikowicz .................. 524/213 |
| 2005/0080150 A1 | 4/2005 | Nakahama et al. |
| 2005/0147655 A1 | 7/2005 | Bagwell |
| 2005/0155687 A1 | 7/2005 | Amaddeo |
| 2006/0014862 A1 | 1/2006 | Dzikowicz |
| 2006/0047269 A1 | 3/2006 | Reever et al. |
| 2006/0059604 A1 | 3/2006 | Lei |
| 2006/0068138 A1 | 3/2006 | Janssen |
| 2006/0099237 A1 | 5/2006 | Modak et al. |
| 2006/0135951 A1 | 6/2006 | Meek et al. |
| 2006/0160922 A1 | 7/2006 | Scott |
| 2006/0173137 A1 | 8/2006 | McGlothlin |
| 2006/0251694 A1 | 11/2006 | Nielsen |
| 2007/0032780 A1 | 2/2007 | Wang |

(56) References Cited

U.S. PATENT DOCUMENTS

| | | |
|---|---|---|
| 2007/0054993 A1 | 3/2007 | Kanz et al. |
| 2007/0054994 A1 | 3/2007 | Kanz |
| 2007/0112313 A1 | 5/2007 | Fangrow |
| 2007/0207186 A1 | 9/2007 | Scanlon |
| 2007/0231522 A1 | 10/2007 | Sakazaki |
| 2007/0287800 A1 | 12/2007 | Acquarulo |
| 2008/0045678 A1 | 2/2008 | Koster |
| 2008/0161452 A1 | 7/2008 | York |
| 2008/0161475 A1 | 7/2008 | York |
| 2008/0173379 A1 | 7/2008 | Mergell |
| 2008/0190322 A1 | 8/2008 | Chen |
| 2008/0221246 A1 | 9/2008 | Imam |
| 2008/0306200 A1 | 12/2008 | Chen |
| 2008/0311409 A1 | 12/2008 | Lipinski |
| 2009/0054551 A1 | 2/2009 | Meissner |
| 2009/0111923 A1 | 4/2009 | Jiang |
| 2009/0176601 A1 | 7/2009 | Snell |
| 2009/0234064 A1 | 9/2009 | Wang et al. |
| 2009/0272384 A1 | 11/2009 | Lucas et al. |
| 2009/0326102 A1 | 12/2009 | Wang et al. |

FOREIGN PATENT DOCUMENTS

| | | |
|---|---|---|
| JP | 1-166310 | 11/1989 |
| JP | 03-031335 | 2/1991 |
| JP | 03031335 A * | 2/1991 |
| JP | 408020675 | 1/1996 |
| JP | 2001-19802 | 1/2001 |
| JP | 2002-282365 | 10/2002 |
| JP | 2004-113474 | 4/2004 |
| JP | 2004-290366 | 10/2004 |
| WO | WO 01/72158 | 10/2001 |
| WO | WO 02/090430 | 11/2002 |
| WO | WO 2005/035589 | 4/2005 |
| WO | WO 2007/017368 | 2/2007 |
| WO | WO 2007/017375 | 2/2007 |

OTHER PUBLICATIONS

JP 03-031335 A (1991), USPTO translation prepared by Phoenix Translations.*

International Search Report and Written Opinion for International application No. PCT/US2008/088526, mailed Feb. 24, 2009.

Dzikowicz, "Latexes," (Vanderbilt Published Articles, Papers and Presentations, Norwalk, CT, R. T. Vanderbilt Co, Inc.), 2003.

* cited by examiner

SYNTHETIC POLYISOPRENE FOLEY CATHETER

RELATED APPLICATION

This application is the National Stage of International Application No. PCT/US2008/088526, filed on Dec. 30, 2008, entitled "SYNTHETIC POLYISOPRENE FOLEY CATHETER," which claims the benefit of U.S. Provisional Application No. 61/019,213, filed Jan. 4, 2008, entitled "SYNTHETIC POLYISOPRENE FOLEY CATHETER," the disclosure of each of which is hereby incorporated by reference in its entirety.

BACKGROUND OF THE INVENTION

1. Field of the Invention

This application relates to indwelling urinary drainage catheters, and relates more specifically to indwelling urinary drainage catheters comprising a hypoallergenic or non-allergenic, synthetic polyisoprene based formulation.

2. Description of the Related Art

Balloon catheters are well known medical devices in which an inflatable member is located adjacent to the distal end medical devices of the catheter shaft and inflated once the catheter is positioned within the body of the patient to anchor the distal end. Such catheters comprise an elongated shaft defining a drainage lumen and an inflation lumen. The drainage lumen comprises a major portion of the cross-section of the catheter shaft and is closed at its distal end by a tip portion. Openings or ports distal to the balloon permit fluid to enter the drainage lumen. The proximal end of the drainage lumen is placed in fluid communication with a method of drainage such as a urinary drainage bag. In some embodiments, the communication is made through a drainage funnel located at the proximal end of the catheter through which the drainage lumen opens.

The inflation lumen is formed within the wall of the catheter shaft and extends from a location inside of the balloon, along the catheter shaft, and through an opening, typically a branch adjacent the proximal end of the shaft. An inflation valve at the end of the branch or other opening permits fluid to be infused into the inflation lumen.

For urinary catheters such as Foley catheters, the catheter is introduced into the patient and is advanced into the urethra until the distal end of the catheter, including the balloon, resides within the bladder. The balloon is then inflated, typically by coupling a syringe to the inflation valve and actuating it to discharge fluid from the syringe, through the inflation lumen, and into the balloon. Foley catheters are typically manufactured from natural rubber latex, or, in some cases, silicone. Natural rubber latex contains proteins that can cause severe allergic reactions in some individuals. Silicone Foley catheters are sometimes used to avoid allergic reactions in such cases.

SUMMARY OF THE INVENTION

An aspect of the invention is directed to a composition comprising synthetic polyisoprene latex and an accelerator system comprising a guanidine. A polyisoprene film formed from heating and curing the composition has a tensile strength of about 3,000 psi to about 5,000 psi.

Another aspect is directed to a composition comprising synthetic polyisoprene latex and an accelerator system comprising a carbamate. A polyisoprene film formed from heating and curing the composition has a tensile strength of about 3,000 psi to about 5,000 psi.

Another aspect is directed to a method for curing synthetic polyisoprene latex that includes forming a film from a composition comprising synthetic polyisoprene latex and an accelerator system having a guanidine and a carbamate as the accelerators. The method further includes heating the film at a temperature of about 50° C. to about 140° C. for about 30 to 240 minutes. The synthetic polyisoprene latex cured film has a tensile strength of about 3,000 psi to about 5,000 psi.

Another aspect is directed to a method for curing synthetic polyisoprene latex that includes forming a film from a composition comprising synthetic polyisoprene latex and an accelerator system having a carbamate and a thiazole as the accelerators. The method further includes heating the film at a temperature of about 50° C. to about 140° C. for about 30 to 240 minutes. The synthetic polyisoprene latex cured film has a tensile strength of about 3,000 psi to about 5,000 psi.

Another aspect is directed to a method for curing synthetic polyisoprene latex that includes forming a film from a composition comprising synthetic polyisoprene latex and an accelerator system having a carbamate, a thiazole and a guanidine as the accelerators. The method further includes heating the film at a temperature of about 50° C. to about 140° C. for about 30 to 240 minutes. The synthetic polyisoprene latex cured film has a tensile strength of about 3,000 psi to about 5,000 psi.

Another aspect is directed to an indwelling urinary drainage catheter formed by the processes disclosed herein.

BRIEF DESCRIPTION OF THE DRAWINGS

These and other features, aspects and advantages of the present invention will now be described in connection with preferred embodiments of the invention, in reference to the accompanying drawings. The illustrated embodiments, however, are merely examples and are not intended to limit the invention. The following are brief descriptions of the drawings.

DETAILED DESCRIPTION OF THE PREFERRED EMBODIMENTS

Figure 1:
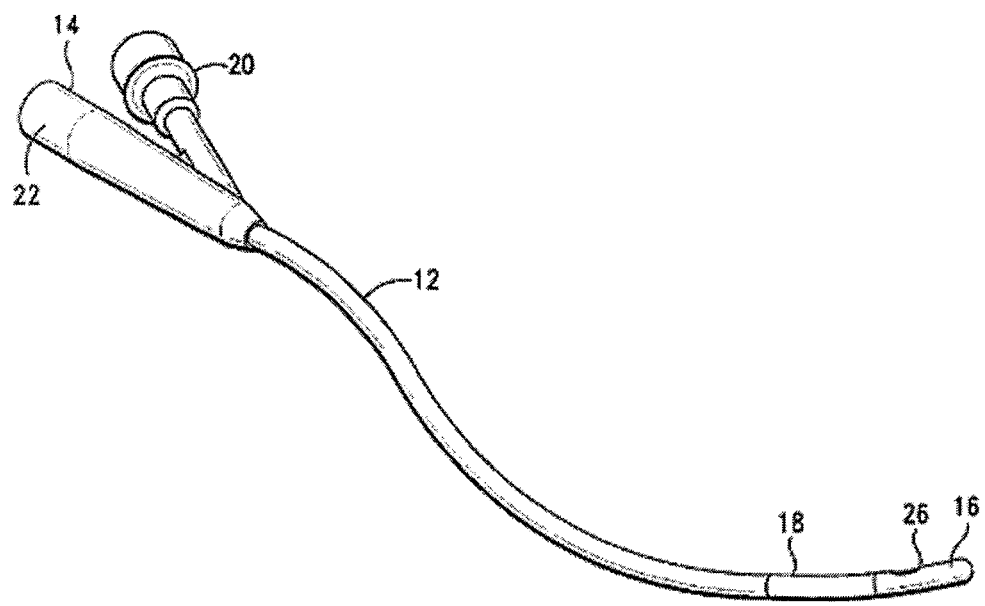
FIG. 1 is a perspective view of a Foley catheter according to a preferred embodiment of the present invention in an uninflated state.

The following detailed description is now directed to certain specific embodiments of the invention. In this description, reference is made to the drawings wherein like parts are designated with like numerals throughout the description and the drawings.

Indwelling urinary drainage catheters, or Foley catheters, typically include a soft, thin rubber tube (or body) with a balloon on one end. The catheter is threaded through the urinary duct (urethra) and into the bladder to drain urine from the bladder. A Foley catheter is typically used when normal urination is disrupted by an infection, a swollen prostate gland, bladder stones, or, sometimes, an injury. In very sick people, a catheter may be used to keep track of urine production.

A typical Foley catheter has a drainage lumen and an inflation lumen for inflating and deflating the balloon. The balloon is normally deflated until properly positioned in a patient's bladder. Once the catheter is properly positioned, the inflation lumen delivers fluid to inflate the balloon. The inflated balloon holds the catheter in place.

Indwelling catheters are predominantly manufactured from natural rubber latex. Silicone catheters are sometimes used to prevent severe (e.g., Type I) allergic reactions caused by the proteins contained in natural rubber latex. Silicone catheters, however, require costly tooling and a complex manufacturing process. In addition, they do not have the same feel, physical properties and versatile processing ability as natural rubber latex. For example, silicone does not have the same elastic properties as natural or synthetic polyisoprene rubber. In addition, the balloon made with silicone rubber does not recover as well as polyisoprene after deflation and can cause discomfort and injury to patients. Furthermore, the stiffness of the silicone catheters required for insertion can increase discomfort to the contact tissues after insertion.

After manufactured, some catheters are dipped in a coating solution so as to be slippery for insertion into the human body. However, conventional coating materials are often not entirely retained on the device surface and can leach out during use, risking toxicity to the patient and decreasing lubricity while in use.

Synthetic polyisoprene latex is a man-made polymer that does not contain natural rubber latex or any other proteins (i.e., allergens). In embodiments of the invention, synthetic polyisoprene can provide a cost-effective substitute to silicone and a hypoallergenic or non-allergenic alternative to natural rubber latex in forming medical articles, such as indwelling urinary drainage catheters. According to various embodiments, synthetic polyisoprene catheters provide the feel and physical properties of natural rubber latex without the risk of natural rubber latex allergic reactions. Also in various embodiments, the recovery of the balloon after deflation is improved, as compared with silicone rubber catheters.

Conventional processes for making elastomeric articles from natural or synthetic latex typically involve preparing a latex dispersion or emulsion, dipping a former in the shape of the article to be manufactured into the latex and curing the latex while on the former. In the curing step, cross-linking or vulcanization through sulfur groups occurs between the polymer units. Certain conventional dipping processes and machinery are applicable to the manufacturing of synthetic polyisoprene catheters. However, conventional compounding formulations and curing conditions used to process natural rubber latex articles are not adequate to produce synthetic polyisoprene articles having the desired properties for certain medical applications, including use in indwelling urinary drainage catheters.

In embodiments of the invention, new compounding formulations and processes are provided to achieve the goal of curing synthetic polyisoprene latex to match the strength of natural rubber latex, while eliminating patient exposure to natural rubber latex protein. Also, in embodiments of the invention, desirable properties of certain elastomeric articles, such as indwelling urinary drainage catheters, can be advantageously influenced or controlled during the cross-linking and curing stages of the manufacturing process. These properties can include, for example, stiffness, tensile strength, and coefficient of friction.

In preferred embodiments of the invention, accelerator systems are provided, including accelerator systems for synthetic polyisoprene latex. The accelerator system is compounded with the synthetic polyisoprene latex and can include one or more accelerators. For example, the accelerator system can include a single accelerator. Exemplary single accelerators include guanidine and carbamate. The accelerator system can include a combination of two accelerators. Exemplary two-accelerator systems can include a combination of guanidine and carbamate or a combination of carbamate and thiazole. An exemplary three-accelerator system can include a combination of guanidine, carbamate and thiazole. The listed accelerator systems are used to produce synthetic polyisoprene having a tensile strength of greater than 3,000 psi to about 5,000 psi. Embodiments of the invention also include methods for curing synthetic polyisoprene latex.

Embodiments of the invention also provide an indwelling urinary drainage catheter having a multi-layered design to render different desired functionalities together. For example, a multilayered article can be produced that has adequate stiffness, along with a low friction coefficient, to enable easy insertion and soft touch in a body to enhance patient comfort. As another example, a first layer of an article can be hydrophobic to facilitate drainage of body fluid and minimize bacterial growth and body fluid residuals retained by the wall of the article. A second layer can be configured to stiffen the article for ease of insertion, and/or can be configured to soften at body temperature so as to reduce pressure on the patient contact tissues. A third layer can comprise tissue repairing nutrients and/or a super absorbent material to reduce drag and friction force for ease in inserting and removal of the article, so as to reduce pain associated with the article during insertion.

In some embodiments, one or more layers of an indwelling urinary drainage catheter can be configured to have a 500% modulus higher than about 500 psi for easy insertion. In some embodiments, synthetic polyisoprene latex is blended with other synthetic polymers or pigments to obtain a 500% modulus up to 500 psi. For example, the synthetic polyisoprene latex may be blended with polyurethane (PU), clay, and/or a polymer filler to achieve the desired material properties. For example, increasing the amount of PU in a given layer generally increases the 500% modulus for that layer.

In an embodiment of an inner or rubberized layer, the synthetic polyisoprene latex is blended with 0-15 phr clay and 0-5 phr polymer filler. In another embodiment of the inner or rubberized layer, the synthetic polyisoprene latex is blended with 0-3 phr PU. In an embodiment of a build up layer, the synthetic polyisoprene latex is blended with 0-15 phr clay, 0-5 phr polymer filler, and 0-3 phr PU. In an embodiment of a finish layer, the synthetic polyisoprene latex is not blended with clay, polymer filler, or PU. With or without blending with other synthetic polymers, the compounded synthetic polyisoprene latex includes the accelerator system described above.

In some embodiments, a finish or outer layer of the catheter is dipped in a slippery, super absorbent material to reduce its coefficient of friction (in a wet condition) to below 0.1 and thereby facilitate easy insertion and removal of the catheter from a patient. In some embodiments, the catheter can be configured to soften within minutes after insertion into the body, to improve patient comfort and reduce the risk of trauma.

Certain preferred embodiments of the invention provide an indwelling urinary drainage catheter having a multi-layer design, with different functional layers bonded together. The references to materials herein as being "bonded" to one another refers to such materials being attached to each other by any means, including but not limited to bonds, attractions, or crosslinks formed between the materials themselves as well as binders or adhesives used to form bonds, attractions, or crosslinks to each material. By such a configuration, the risk of chemicals leaching out can be reduced or minimized.

Figure 2:
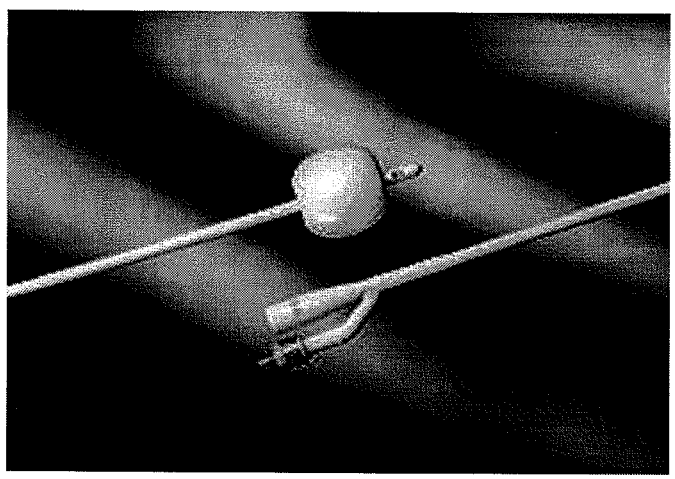
FIG. 2 is a plan view of a Foley catheter similar to the catheter from FIG. 1 with a balloon portion of the catheter in an inflated state.

FIG. 1 is a perspective view of a Foley catheter according to a preferred embodiment of the present invention in an uninflated state. The catheter includes a catheter body 12 with a proximal end 14 and a distal end (or tip) 16. The catheter also includes a balloon 18, an inflation lumen 20, and a drainage lumen 22. The balloon 18 is deflated for insertion into a patient. The balloon 18 is disposed near the distal end 16. The inflation lumen 20 extends within the catheter body 12 from the proximal end 14 to the balloon 18, in fluid communication with the balloon 18, for inflating and deflating the balloon 18. FIG. 2 shows another Foley catheter with an inflated balloon.

The catheter drainage lumen 22 extends from the proximal end 14 to the distal end 16. The distal end 16 includes an opening 26 in fluid communication with the drainage lumen 22 to facilitate drainage of urine from the bladder of a patient.

The Foley catheter illustrated in FIG. 1 comprises synthetic polyisoprene rubber (SPIR). Stereoregular polyisoprene can be synthesized using various catalyst systems to selectively join together monomer units in a well-ordered fashion. The resulting synthetic polyisoprene rubber (SPIR) tends to exceed natural latex rubber in product consistency, cure rate, and purity. SPIR also exhibits superior characteristics in mixing, extrusion, molding, and calendaring processes. SPIR can be manufactured to meet the particular tensile and resiliency requirements of Foley applications, while avoiding the risk of allergic reaction in sensitive patients.

Part or all of the Foley catheter can comprise SPIR. For example, the body 12, the inflation lumen 20, the drainage lumen 22, the balloon 18, and/or the catheter tip 16 can comprise SPIR. These parts can be formed by extrusion and/or by molding processes, such as injection molding. The SPIR can comprise cis-1,4-polyisoprene, trans-1,4-polyisoprene, or can have a primarily 1,2 or 3,4 structure. The SPIR can also be crosslinked or otherwise treated to produce the desired characteristics for Foley applications.

Figure 3:
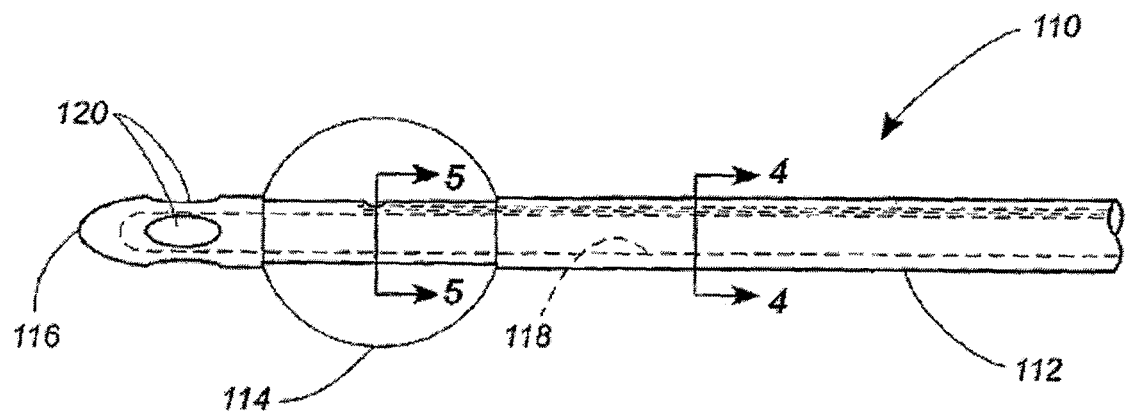
FIG. 3 is a side view of a balloon catheter according to an embodiment of the present invention.

Referring now to FIG. 3, a catheter 110 comprises an elongated catheter shaft 112. A balloon 114 is located adjacent the forward tip 116 of the catheter shaft 112. A drainage lumen 118 extends longitudinally within the catheter shaft 112 and terminates just short of the tip 116. The drainage lumen 118 is in communication with the ambient surrounding the tip 116 by way of a plurality of radial drainage eyes 120.

Figure 4:
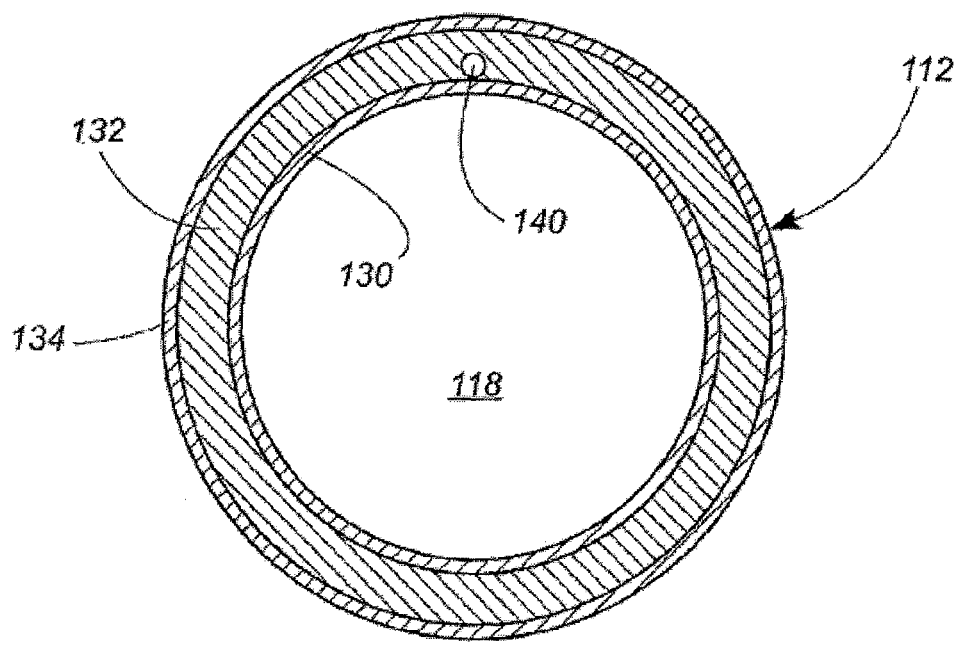
FIG. 4 is a cross-sectional view taken along line 4-4 of FIG. 3.

FIG. 4 is a cross-sectional view of the catheter shaft 112 as seen along line 4-4 of FIG. 3. Embodiments of the catheter shaft 112 are formed from two or more distinct layers. The catheter shaft 112 illustrated in FIG. 3 is formed from three distinct layers: an innermost or rubberize layer 130, an intermediate or build up layer 132, and an outermost or finish layer 134. In an exemplary two layer embodiment, the finish layer is omitted. Formed within the build up layer 132 and having its lower edge in contact with the rubberize layer 130 is an inflation lumen 140.

Figure 5:
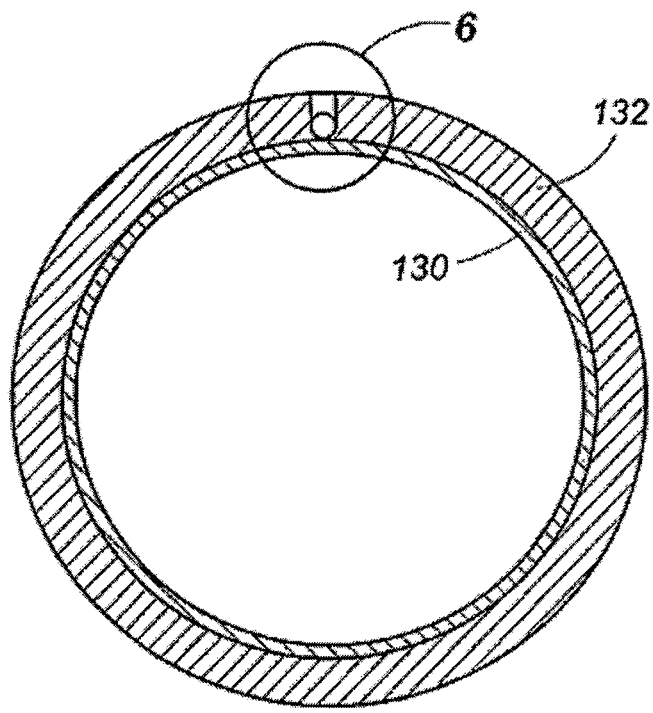
FIG. 5 is a cross-sectional view taken along line 5-5 of FIG. 3 with an expanded finish layer omitted for clarity.
Figure 6:
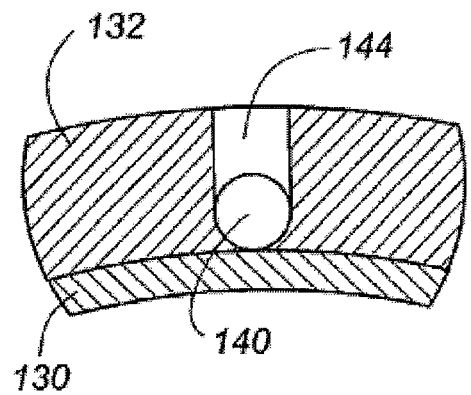
FIG. 6 is an enlarged view of an upper portion of FIG. 5 designated by view 6.

FIG. 5 is a cross-sectional view of the catheter shaft 112 as seen along line 5-5 of FIG. 3. Not seen in FIG. 5, the finish layer 134 is expanded away from the build up layer 132 as the balloon 114 is inflated, leaving only the rubberize layer 130 and build up layer 132 visible. FIG. 6 is an enlarged view of an upper portion from FIG. 5 designated by view 6 and shows the inflation lumen 140 and an inflation eye 144. The inflation eye 144 may be arranged in a radial direction. The inflation eye 144 places the inflation lumen in communication with the space between the build up layer 132 and the balloon 114.

The relative stiffnesses of the various layers 130, 132, and 134 of the balloon catheter 110, as expressed by their Young's moduli, can be controlled. The catheters of the present invention can include an inner rubberize layer 130 of material having a Young's Modulus that is higher than the Young's Modulus of the middle layer 132. In some embodiments having both a middle layer 132 and an outer layer 134, the Young's Modulus of the inner layer can be higher than that of both the middle layer 132 and the outer layer 134. As used herein, Young's Modulus refers to the Modulus of Elasticity when determined according to standard procedures such as American Society for Testing and Materials (ASTM) Method E-111-82 using sample preparation procedures set forth in ASTM Method D-412-98a. As used herein, "wet" Young's Modulus shall refer to Young's Modulus measured after immersion of a material in deionized water at a temperature of 60-85° F. for a period of 4-5 days. As used herein, "dry" Young's Modulus shall refer to Young's Modulus of a material that has not been immersed.

In some embodiments, a coagulant dipping process is used to produce elastomeric articles from synthetic polyisoprene. An article-shaped mold is first dipped into a coagulant solution which is known to destabilize the latex. The coagulant dipped mold is then dried and dipped in compounded synthetic polyisoprene. Other synthetic materials such as calcium stearate, magnesium stearate, zinc stearate, polyethylene, polybutadiene emulsion, styrene-isoprene-styrene block copolymer emulsion, polyacrylate, polyurethane, polychloroprene, styrene/butadiene copolymer, nitrile latex and the like can be successfully blended as part of the compounded synthetic polyisoprene latex. The coagulant dip and the polyisoprene latex dip can be dipped multiple times to build up appropriate thickness required for serving different functionalities of elastomeric articles (or layers thereof). The coagulated wet gel on the mold is submersed in water to leach out the residual compounding ingredients and the coagulant. After the leaching process the wet gel on the mold can be placed in an oven at a temperature range from, for example, 50° to 140° C. After staying in the oven for a specific time, the mold is removed and cooled down. Finally, the articles are stripped from the mold.

In one embodiment, an elongated rod or "form" is dipped into a first liquid coating material to form a layer of coating material on the form. The form has the shape and dimensions of the drainage lumen 118 of the catheter. This first coating layer forms the inner or rubberize layer 130 of the catheter. Once the first layer 130 has dried, an elongated wire is attached longitudinally to the outside of the first layer 130. The form with first layer 130 and wire is then dipped into a second coating material to build up an intermediate or build up layer 132. Multiple dips into the second coating material may be necessary to build up an intermediate layer 132 of appropriate thickness. The inflation eye 144 is then formed near the distal end of the second layer 132 to place the inflation lumen 140 in communication with the ambient surrounding the second layer 132. The build up layer 132 is then dried. The finish layer 134 is applied with a subsequent dip and is dried.

The balloon 114 can be formed in a number of ways, and any method for forming the balloon may be used. In some preferred embodiments, the balloon is formed by the application of a pre-formed balloon component on the second layer 132. In one of these embodiments, a finish layer 134 is used and is applied over the pre-formed balloon component and thus forms part of the wall of the balloon 114. In another of these embodiments, no finish layer 134 is used and the pre-formed balloon component forms the entire wall of the balloon 114. In other embodiments, a masking material is applied to the exterior of the second layer 132 in the balloon formation area such that a bond does not form between the build up layer 132 and the finish layer 134 in the area surrounding the inflation eye 144 of the inflation lumen 140. In such latter embodiments, the unadhered portion of the finish layer 134 becomes the inflatable balloon 114.

Regardless of the method used to form the balloon 114, the form with first and second layers 130, 132 and the balloon formation is then dipped into a third coating solution to build up the outer or finish layer 134. Once the outer layer 134 has been dried, the catheter 110 is removed from the form. The space formerly occupied by the form and the inflation wire become the drainage and inflation lumens 118 and 140, respectively. Drainage eyes 120 are then formed in the catheter shaft 112 adjacent its distal end 116 to place the drainage lumen 118 in communication with the ambient surrounding the forward end of the shaft 112. The balloon 114 is inflated by infusing an inflation medium out the inflation eye 144 of the inflation lumen 140 and into the balloon 114.

To introduce an uninflated balloon catheter 110 into a patient, a stylet may be inserted into the proximal end opening of the drainage lumen (for example, the opening of a drainage funnel) of the catheter and advanced until the forward end of the stylet bears against the inside of the forward tip 116 of the catheter. The catheter 110 with the stylet affixed is then advanced through the urethra and into the neck of the bladder. Because all of the force drawing the catheter 110 along into place is being exerted against a single point in the tip 116 of the catheter 110, it has typically been necessary to embed a fabric reinforcement cap within the wall of the catheter tip 116 to spread out the forces exerted by the stylet over a greater area of the catheter tip 116. In some embodiments, the innermost layer 130 of the catheter 110 is stiffened so that it is able to withstand the forces exerted upon it by the stylet tip without the need for reinforcement, thereby eliminating the need for the embedded fabric and thus substantially simplifying construction.

Figure 7:
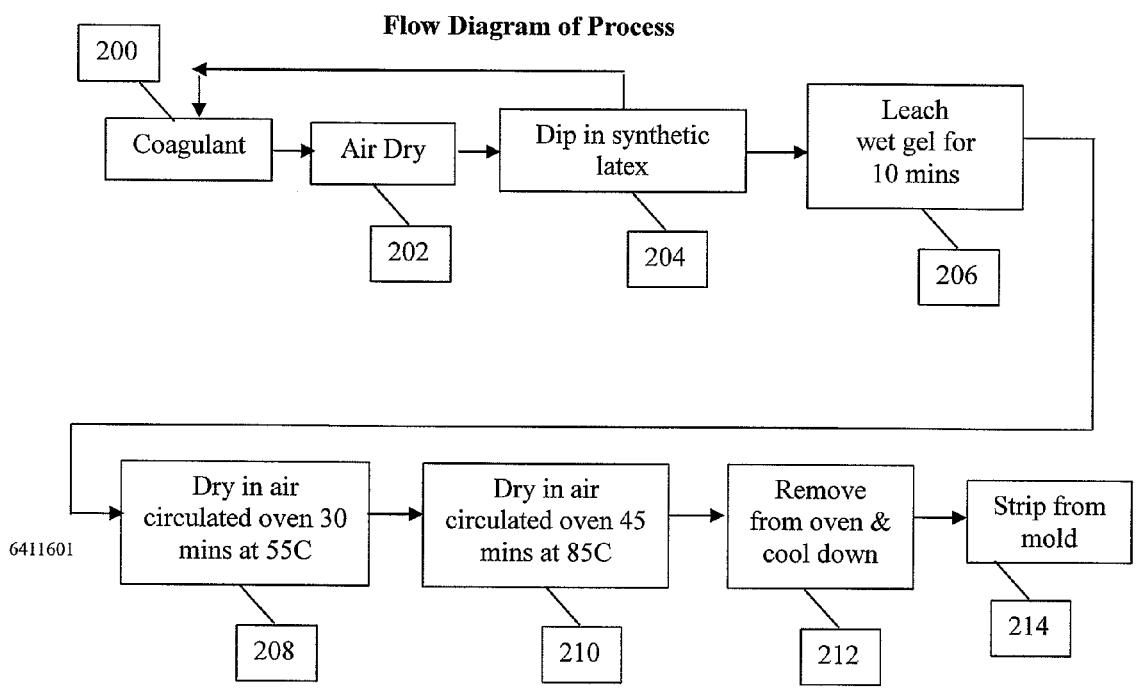
FIG. 7 is a block diagram describing an exemplary process for manufacturing a Foley catheter, according to a preferred embodiment of the present invention.

FIG. 7 is a block diagram describing an exemplary process for manufacturing a Foley catheter, according to a preferred embodiment of the present invention. The process begins with a mold being dipped in a coagulant 200. One example of a suitable coagulant is a solution comprising, for example, 40 gram of calcium nitrate, 8 grams of calcium carbonate and 52 grams of water. Next at block 202, the dipped mold is air dried.

Exemplary compounds of synthetic latex for use in block 204, including an accelerator system, are set forth below. To prepare the synthetic latex for use in block 204, the compound is heated to specific temperature for a specified time. Exemplary cook profiles include, from 1 to 4 hours at 100 F with a 4.75 hour cool down. Another exemplary profile includes 1 hr at 100 F. Another exemplary profile includes 1-2 hours at 90F.

The mold is dwelled in the compounded polyisoprene latex for, for example, 1-7 minutes, preferably 2-5 minutes at block 204. Blocks 200, 202, and 204 may be repeated as needed depending on desired geometry and properties of the medical article or layer.

Next, at block 206, the gel film can be leached in water for, for example, 10 minutes. The mold is then dried in one or more steps. For example, the mold may be dried in an air-circulated oven for 30 minutes at 55° C. at block 208 and then dried in an air-circulated oven for 45 minutes at 85° C. at block 210. At block 212, the dried mold is removed from the oven and cooled. After cooling, the medical article is striped from the mold at block 214.

The following examples set forth different compounds of synthetic latex which can be compounded for use in block 204 of FIG. 7. Each compound of synthetic latex includes an accelerator system. The accelerator system compositions listed below are exemplary and should not be construed as limiting the claims to the embodiments depicted therein. Further, different accelerator systems may be used for different layers of a multi-layer medical article.

EXAMPLE 1

Synthetic polyisoprene latex was prepared with the compounding ingredients listed below in Table 1 and then evaluated. The components are reported by weight as parts per hundred. Diphenyl guanidine was the only accelerator used in the range of 0.1 to 2 phr, preferably 0.2 to 1.0 phr.

The typical curing conditions were 30 minutes at 55° C. and then 45 minutes at 85° C. The physical properties were evaluated using an Instron 5564 and measured according to ASTM D-412. The products prepared in this manner exhibited physical properties as follows: 3541 psi for tensile strength, 1075% elongation at break and 237 psi for 500% modulus. This example illustrates that articles prepared with only a guanidine accelerator can exhibit tensile strength greater than 3000 psi.

TABLE 1

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Preferred Sulfur | 2 |
| Sulfur donor | 1 |
| Diphenyl guanidine | 0.5 |
| Zinc oxide | 1.5 |
| 2,2'-methylenebis (4-ethyl-6-tertiarybutyl phenol) | 2.0 |

EXAMPLE 2

Synthetic polyisoprene latex was prepared with the compounding ingredients listed below in Table 2 and then evaluated. A combination of diphenyl guanidine (DPG) and sodium dibutyl dithiocarbamate (SBC) accelerators was used. DPG ranged from about 0.1 to 2 phr, preferably 0.2 to 1 phr. SBC ranged from about 0.01 to 2 phr, preferably 0.025 to 1.0 phr. The typical curing conditions were 30 minutes at 55° C. and then 45 minutes at 85° C. The products prepared in this manner exhibited physical properties as follows: tensile strength of 3356 psi, 983% elongation at break, and 500% modulus of 337 psi. This example illustrates that articles prepared with guanidine and carbamate accelerators can exhibit tensile strength greater than 3000 psi.

TABLE 2

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Preferred Sulfur | 2 |
| Sulfur donor | 1 |
| Diphenyl guanidine | 0.5 |
| Sodium dibutyl dithiocarbamate | 0.25 |
| Zinc oxide | 1.5 |
| 2,2'-methylenebis (4-ethyl-6-tertiarybutyl phenol) | 2.0 |

EXAMPLE 3

Synthetic polyisoprene latex was prepared with the compounding ingredients listed below in Table 3 and then evaluated. Sodium dibutyl dithiocarbamate was the only accelerator used in the range of 0.01 to 2 phr, preferably 0.025 to 0.5 phr. The typical curing conditions were 30 minutes at 55° C. and then 45 minutes at 105° C. The products prepared in this manner exhibited physical properties as follows: tensile strength of 3898 psi, 960% elongation at break, and 500% modulus of 328 psi. This example illustrates that articles prepared with only a carbamate accelerator can exhibit tensile strength greater than 3000 psi.

TABLE 3

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Preferred Sulfur | 2 |
| Sulfur donor | 1 |
| Sodium dibutyl dithiocarbamate | 0.1 |
| Zinc oxide | 1.5 |
| 2,2'-methylenebis (4-ethyl-6-teriarybutyl phenol) | 2.0 |

EXAMPLE 4

Synthetic polyisoprene latex was prepared with the compounding ingredients listed below in Table 4 and then evaluated. About 0.1 to 2 phr of zinc mercaptobenzothiazole (ZMBT) and about 0.05 to 2 phr of zinc diethyl dithiocarbamate (ZEC) are the accelerators used. The preferable range for ZMBT is 0.25 to 1.5 phr and for ZEC 0.05 to 1 phr. The typical curing conditions were 30 minutes at 120° C. The products prepared in this manner exhibited physical properties as follows: tensile strength of 3266 psi, 1098% elongation at break, and 500% modulus of 288 psi. This example illustrates that articles prepared with a combination of thiazole and carbamate accelerators can exhibit tensile strength greater than 3000 psi.

TABLE 4

| Compounding Ingredients | Parts per hundred rubber |
|---|---|
| Synthetic polyisoprene latex | 100 |
| Ammonium Hydroxide | 0.2 |
| Sulfur or sulfur donor or a combination | 1-4 |
| Preferred Sulfur | 2 |
| Sulfur donor | 1 |
| Zinc diethyl dithiocarbamate | 0.25 |
| Zinc mercaptobenzo thiazole | 0.5 |
| Zinc oxide | 1.5 |
| Hindered phenol | 0.5 |

EXAMPLE 5

Synthetic polyisoprene latex was prepared with the compounding ingredients listed below in Table 5 and then evaluated. About 0.1 to 2 phr of zinc mercaptobenzothiazole (ZMBT), about 0.05 to 2 phr of diphenylguanidine (DPG), and about 0.05 to 2 phr of sodium dibutyl dithiocarbamate (SBC) are the accelerators used. The typical curing conditions were 45 minutes at 115° C. The products prepared in this manner exhibited physical properties as follows: tensile strength of 3161 psi, 863% elongation at break, and 500% modulus of 387 psi. This example illustrates that articles prepared with a combination of thiaole, carbamate and guanidine accelerators can exhibit tensile strength greater than 3000 psi.

TABLE 5

| Compounding Ingredients | Parts per hundred rubber |
|---|---|
| Synthetic polyisoprene latex | 100 |
| Potassium hydroxide | 0.2 |
| Sulfur or sulfur donor or a combination | 1-4 |
| Preferred Sulfur | 2 |
| Sulfur donor | 1 |
| Sodium dibutyl dithiocarbamate | 0.1 |
| Zinc mercaptobenzo thiazole | 0.5 |
| Diphenyl guanidine | 0.25 |
| Zinc oxide | 1.5 |
| Hindered phenol | 0.5 |

The various embodiments of SPIR Foley catheters described above thus provide a number of advantages over known Foley catheters. Of course, it is to be understood that not necessarily all such objectives or advantages may be achieved in accordance with any particular embodiment of the SPIR Foley catheter described herein. Thus, for example, those skilled in the art will recognize that the SPIR Foley catheter may be developed in a manner that achieves or optimizes one advantage or group of advantages as taught herein without necessarily achieving other objectives or advantages as may be taught or suggested herein.

It is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A composition comprising synthetic polyisoprene latex and an accelerator system comprising a carbamate as the only accelerator in the range of 0.01 phr to 0.1phr, wherein a polyisoprene film formed from heating and curing the composition has a tensile strength of about 3,000 psi to about 5,000 psi.

2. The composition of claim 1 wherein the carbamate is sodium dibutyl dithiocarbamate.

3. The composition of claim 2 wherein the amount of sodium dibutyl dithiocarbamate is about 0.1 phr.

4. The composition of claim 1, wherein the polyisoprene film is formed by heating the composition for 30 minutes at 55° C. and then for 45 minutes at 105° C.

5. The composition of claim 1, further comprising sulfur.

6. The composition of claim 5, wherein the amount of sulfur is between about 1 phr and 4 phr.

7. The composition of claim 5, wherein the ratio of sulfur to carbamate is between about 40:1 and 10:1.

8. The composition of claim 7, wherein the ratio of sulfur to carbamate is 20:1.

9. The composition of claim 1, further comprising zinc oxide.

10. The composition of claim 9, wherein the amount of zinc oxide is 1.5 phr.

* * * * *

UNITED STATES PATENT AND TRADEMARK OFFICE
CERTIFICATE OF CORRECTION

PATENT NO. : 8,633,268 B2  
APPLICATION NO. : 12/811439  
DATED : January 21, 2014  
INVENTOR(S) : Kenneth Glenn Lawson et al.

Page 1 of 1

It is certified that error appears in the above-identified patent and that said Letters Patent is hereby corrected as shown below:

In the Specification

At Column 9, Line 40, please change "teriarybutyl" to --tertiarybutyl--.

At Column 10, Line 25, please change "thiaole," to --thiazole,--.

In the Claim

At Column 10, Line 67, in Claim 1, please change "0.1phr," to --0.1 phr,--.

Signed and Sealed this  
Twenty-third Day of September, 2014

Michelle K. Lee  
*Deputy Director of the United States Patent and Trademark Office*